United States Patent [19]

O'Reilly et al.

[11] Patent Number: 4,874,876

[45] Date of Patent: Oct. 17, 1989

[54] PROCESS FOR THE PREPARATION OF 2-(2-THIENYL)-ETHYLAMINE AND DERIVATIVES THEREOF

[75] Inventors: Neil J. O'Reilly; Henry C. Lin, both of Grand Island, N.Y.

[73] Assignee: Occidental Chemical Corporation, Niagara Falls, N.Y.

[21] Appl. No.: 265,980

[22] Filed: Nov. 2, 1988

[51] Int. Cl.$^4$ ............................................. C07D 333/58
[52] U.S. Cl. ......................................... 549/49; 549/74
[58] Field of Search .................. 549/74, 49, 492, 462; 564/377, 375, 374

[56] References Cited

U.S. PATENT DOCUMENTS 3,767,659  10/1973  Suh et al. ........................... 549/49 X
3,910,955  10/1975  Chapman et al. ...................... 549/49
4,181,738  1/1980   Ginos et al. ....................... 564/375 X Primary Examiner—Richard A. Schwartz
Assistant Examiner—E. B. Magrab
Attorney, Agent, or Firm—James F. Tao; Arthur S. Cookfair

[57] ABSTRACT

The present invention provides a process for the preparation of 2-(2-thienyl)-ethylamine and derivatives thereof having the general formula:

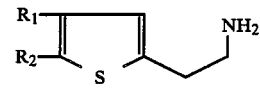

wherein $R_1$ and $R_2$ are hydrogen or taken together form a phenyl ring.

9 Claims, No Drawings

PROCESS FOR THE PREPARATION OF 2-(2-THIENYL)-ETHYLAMINE AND DERIVATIVES THEREOF

BACKGROUND OF THE INVENTION

The present invention is concerned with new processes for the preparation of 2-(2-thienyl)-ethylamine and derivatives thereof having the following formula:

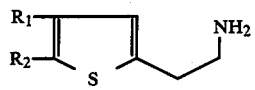

wherein $R_1$ and $R_2$ are hydrogen or taken together form a phenyl ring. Some of the compounds of formula I have already been prepared according to a variety of methods including reduction of 2-Ω-nitrovinyl-thiophene with lithium aluminum hydride [S. Gronovitz & Sandberg, *Arkiv. for Kemi*, (1970), 32, 217; M. L. Dressler, M. Soullie, *J. Het. Chem.*, (1970), 7, 1257]. They have also been prepared from 3-(2-thienyl)-propionamide, by means of a Hoffman degradation reaction [G. Barger, A. Easson, *J. Chem. Soc.*, (1938), 2100]. Another method features reduction of 2-cyahomethyl thiophene with lithium aluminum hydride [B. F. Growe, F. F. Nord, *J. Org. Chem.*, (1950), 15, 81; J. W. MacFarland, H. L. Howes, *J. Med. Chem.*, (1969), 12, 1079]. These compounds have also been prepared by transamination of phthalimide derivatives as displayed in U.S. Pat. No. 4,128,561 to Braye. However, such prior methods either do not provide compounds of the formula (I) in sufficient yields, or require the use of dangerous or expensive chemicals, such as lithium aluminum hydride.

Consequently, the object of the present invention is to provide an inexpensive industrial synthesis process which will produce 2-(2-thienyl)-ethylamine and derivatives thereof of the aforementioned formula (I) in improved yields.

The subject compounds, 2-(2-thienyl)-ethylamine and derivatives thereof, are known compounds used as intermediates in the synthesis of a large number of products used in both the chemical and pharmaceutical industries. Of particular interest is the anti-arhythmic drug ticlopidine.

The process according to the instant invention comprises acylating a thiophene compound of the formula:

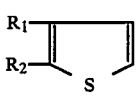

in which $R_1$ and $R_2$ are as defined in formula (I); and subsequently reducing and hydrolyzing the intermediate product.

According to one embodiment of the present invention the acylation is carried out by adding a compound of the formula (11) to a mixture of an acylation catalyst such as $AlCl_3$ and an acylating compound of the formula III or IV:

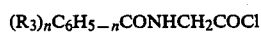

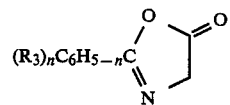

wherein $R_3$ is selected from the group consisting of $C_{1-4}$ lower alkyl, $C_{1-4}$ lower alkoxy, phenoxy, $NO_2$, $CF_3$, Cl, Br, I and F, and n=0 to 3.

Preferable acylating compounds for use in the present invention include formula III - hippuryl chloride and formula IV -2-phenyl-5-oxazolone (Lancaster Synthesis) wherein n=0 for each compound respectively.

It is an important feature of the present invention to premix the catalyst with the acylating compound (III or IV) prior to the addition of the thiophene compound (11) to the mixture. This premixing provides greatly improved yields in the resultant product and is the inverse of that typically taught in the literature. This is demonstrated in the following table:

| Acylating Agent | Order of Addition AlCl₃ First (Inverse) | AlCl₃ Last (Normal) |
|---|---|---|
| Hippuryl Chloride | 37.6–49.8% Yield | 20.9% Yield |
| 2-phenyl-5-oxazolone | 47.3–52.1% Yield | 38.8% Yield |

The acylation catalyst is necessarily an acid catalyst, preferably a Lewis acid catalyst, such as $AlCl_3$, $SnCl_4$, $AlBr_3$, $BF_3$, and the like, all of which are capable of promoting a Friedel-Crafts type reaction.

Suitable inert solvents for conducting the acylation reaction include any solvent suitable for Friedel-Crafts reactions, for example: methylene chloride, nitromethane, carbon disulfide, nitro benzene, 1,2-dichloroethane and the like.

The acylation reaction is carried out in any suitable temperature range between the freezing and boiling points of the solvent, preferably from 0° C. to room temperature.

The acylated compound produced from the reaction of compound (II) with a compound of either formula III or IV is represented by the formula:

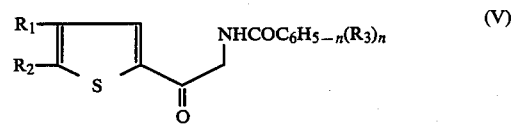

wherein $R_1$, $R_2$, $R_3$, and n are defined above.

The preferred acylated compound (V) prepared in accordance with the instant invention is α-N-benzoylamino-2-acetylthiophene as represented by the formula (V) where $R_1$ and $R_2$ are hydrogen and n=0.

The intermediate product of formula (V) is subsequently reduced and hydrolyzed to produce the compounds of the instant invention, namely, 2-(2-thienyl)-ethylamine derivatives of formula (I).

Typically hydrolysis is carried out utilizing an acid having a concentration from 5 to 100% such as HCl, $H_2SO_4$, and the like but dilute bases such as NaOH may also be employed. The hydrolysis reaction is performed at temperatures ranging from ambient to the boiling point of solvent which is preferably water. Hydrolysis of compound (V) cleaves the benzoyl group to form a resultant pendent amino group on the thienyl derivative.

The acylated product (V) is reduced by reduction of the ketone substituent utilizing a variety of reducing conditions in accordance with procedures in the following articles which represent the state-of-the-art.

| Conditions | Reference |
| --- | --- |
| KOH/NH$_2$NH$_2$ (HOCH$_2$CH$_2$)$_2$O | Gooman, M. M., Kirsch, G. and Knapp, Jr., F. F. J. Med. Chem., (1984), 2, 390. See also J. Amer. Chem. Soc., (1946), 69, 2487; Organic Reaction, (1948), 378. |
| NH$_2$NH$_2$; then KOt—Bu/DMSO or THF | Cram, D. J., Sahyun, M. R. V., and Knox, G. R., J. Amer. Chem. Soc., (1962), 84, 1734. |
| NH$_2$NH$_2$; then KOt—Bu/toluene | Grundon, M. F. et al. J. Chem. Soc., (1963), 1855. |
| HSCH$_2$CH$_2$SH/Ra—Ni | Sobti, R. R. and Dev. S. Tetrahedron, (1970). 26, 649. |
| TFA/NaBH$_4$ | Gribble, G. W. et al, Synthesis (1978), 763; J. Org. Chem., (1978) 43, 2299. |
| AlCl$_3$/LAH | Brown, B. R. and White, A. M. S., J. Chem. Soc., (1957), 3755; Blackwel, J. and Hickinbottom, W. J., J. Chem. Soc. Chem. Commun. (1969). 919. |
| Zn/HCl(g) | Yamamura, S. et al, J. Chem. Soc., Chem. Commun., (1969), 919. |
| Zn/NH$_3$CuSO$_4$ | J. Org. Chem., (1970), 35, 711. |
| Ni—Al/NaOH/H$_2$O | Organic Reactions, (1953), 7, 263. |
| Et$_3$SiH/TFA (or BR$_3$) | Tetrahedron, (1967), 23, 2235; J. Org. Chem., (1978), 43, 374. |

Preferably, the reduction step is conducted in a nonpolar, aprotic solvent such as diethyl ether, tetrahydrofuran or dioxane. Hydrogen chloride gas is preferably used as the reducing agent in the presence of zinc powder.

It is preferably but not necessary to perform the reduction of acylated compound (V) prior to the hydrolysis to restrict pyrazine formation. However, under basic conditions, e.g., a Wolff-Kischner reduction using hydrazine and an appropriate base, such as KOH, it is possible to carry out reduction and hydrolysis simultaneously. Other suitable bases include NaOH, NaH, and potassium tert-butoxide. This reaction can be conducted in polar protic or aprotic solvents as well as a polar solvents at a temperature between ambient and the boiling point of the solvent which is being utilized in the system.

The following examples illustrate, but do not limit the invention.

The following examples employed the procedures. Melting points were determined on a Buchi 510 melting point apparatus and are uncorrected. $^1$H and $^{13}$C NMR spectra were recorded on an IBM-Brucker AC-300 spectrometer. Mass spectra were recorded on either Finnigan MAT 212 or 4500, or Hewlett-Packard 5985 mass spectrometers. Reactions were followed using a combination of DB-5 capillary column on a Hewlett-Packard 5890 GC and TLC on silica coated glass plates eluting with methanol/chloroform mixtures, the spots being visualized by UV and iodine staining.

Chemicals were purchased from the Aldrich Chemical Company and were used without further purification. Solvents were J. T. Baker analytical grade. Methylene chloride was refluxed over calcium hydride in a dry nitrogen atmosphere and distilled prior to use. NMR internal standard (ISTD) purity determinations employed 2-methoxynaphthalene as the added standard, and involved a comparison of the peak areas of the methylene peak of the product with the methoxy peak of the standard.

EXAMPLE 1

Preparation of Hippuryl Chloride

The title compound was prepared by the chlorination of hippuric acid using phosphorus pentachloride in acetyl chloride according to a literature procedure, mp 124°–126° C. dec (McInally, I. et al *J. Polymer Sci. Polymer Chem. Ed.* (1977), 15, 2511, mp 125° C. dec.).

EXAMPLE 2

Preparation of 2-Phenyl-5-oxazolone

The title compound was prepared by the dehydration of hippuric acid with acetic anhydride according to the procedure of Bullerwell and Lawson, [*J. Chem. Soc.* (1952), 1350], mp 91.5°–93.5° C. (lit. 91° C).

EXAMPLE 3

Acylation of Thiophene With Hippuryl Chloride

A 500 mL, round-bottomed, 3-necked flask was charged with 19.76 g (99.99 mmol) of hippuryl chloride, and 200 mL of dried methylene chloride, and cooled in an ice bath under a dry nitrogen atmosphere. Using a powder addition funnel, 40.01 g (0.3 mol, 3.0 equiv.) of aluminum chloride was added over a period of 25 minutes to the stirred reaction mixture, and the resulting solution was stored at 0° C. over the week-end (68 hours). Thiophene (9.6 mL, 119.91 mmol) was added over a 37 minute period with the temperature maintained below 4° C. The reaction mixture was then stirred 4.6 h with ice bath cooling, followed by 1.5 hours at room temperature, and finally 6 hours under reflux. After cooling to room temperature the reaction was quenched with ice water (200 mL) and extracted with 3×100 mL of methylene chloride. The combined extracts were dried over anhydrous sodium sulfate, filtered, and then stripped on a rotary evaporator. The resulting crude product (19.34 g) was recrystallized from hot methanol (500 mL) with activated carbon treatment, and the resulting product was dried in a vacuum desiccator The yield of α-N-benzoylamino-2-acetylthiophene as a tan/beige solid was 43.8% (10.74 g); mp 148.5°–152° C. (Moriya, T. et al *J. Med. Chem.* (1986), 29, 333, mp 146°–147° C.). Re-work of the stripped mother-liquor afforded a second crop (mp 146.5°–150° C.), bringing the total isolated yield to 49.8%. The $^1$H and $^{13}$C NMR spectra were in agreement with the expected structure.

EXAMPLE 4

The reaction of Example 3 was repeated with 2.0 equiv. of AlCl$_3$. A 37.6% yield was determined by NMR/ISTD analysis of the crude α-N-benzoylamino-2-acetylthiophene product.

EXAMPLE 5

Acylation of Thiophene With 2-Phenyl-5-oxazolone

A 500 mL, round-bottomed, 3-necked flask was charged with 23.0 g (142.7 mmol) of 2-phenyl-5-oxazolone, and 250 mL of dried methylene chloride, and cooled in an ice bath under a nitrogen atmosphere. Using a powder addition funnel, 57.0 g (3.0 equiv.) of aluminum chloride was added over a period of 1 hour to the stirred reaction mixture. After holding for 20 minutes the gradual addition of thiophene (14.4 mL, 1.22 equiv.) was carried out over a 1 hour period. The reaction mixture was then stirred overnight (15 hours) at room temperature, and the reaction was then quenched by the addition of iced water. The product was extracted several times with methylene chloride, and the combined extracts were dried over anhydrous sodium sulfate, filtered, then stripped on a rotary evaporator. After drying at the pump the crude product (33.96 g) was recrystallized from hot methanol with activated charcoal treatment to yield 14.77 g (42.2%) of α-N-benzoylamino-2-acetylthiophene was a white solid; mp 153°–154° C. Re-work of the mother liquor afforded a second batch of product (mp 140°–146° C.), bringing the total yield of product to 47.3%.

EXAMPLE 6

The reaction of Example 5 was repeated with 2.0 equiv. of AlCl$_3$. A 52.1% yield was determined by NMR analysis of the crude α-N-benzoylamino-2-acetylthiophene product.

EXAMPLE 7 - (COMPARATIVE)

Attempted Acylation of Thiophene With Hippuryl Chloride With Normal Catalyst Addition In Nitromethane A 25 mL, round-bottomed, 2-necked flask was charged with 1.23 g of hippuryl chloride (6.2 mmol), 5 mL of nitromethane (dried over A4 molecular sieves), and 0.5 mL of thiophene (6.2 mmol). To the stirred reaction mixture was added a solution of aluminum chloride (1.70 g, 12.7 mmol) in nitromethane (2 mL), over a period of 2 minutes. The reaction mixture was stirred at room temperature for 3 hours, and then heated to 60° C. for 17 hours. GC analysis of a water quenched sample after this time indicated hippuryl chloride to be the major component, with a small amount of thiophene present. No acylation product was observed.

EXAMPLE 8 - (COMPARATIVE)

Acylation of Thiophene With Hippuryl Chloride With Normal Catalyst Addition In Methylene Chloride A 500 mL, round-bottomed, 3-necked flask was charged with 10.03 g (50.75 mmol) of hippuryl chloride, 5.1 mL (63.7 mmol, 1.26 equiv.) of thiophene, and 200 mL of dried methylene chloride. The cream-colored slurry was stirred under a nitrogen atmosphere with ice bath cooling for 25 minutes. The gradual addition of 13.49 g (1.99 equiv.) of aluminum chloride was then carried out over a 1 hour period. After 2 hours at 2° C. the reaction was heated under reflux for 1.5 hours. An additional 0.5 mL (6.25 mmol, 0.12 equiv.) of thiophene was then added and the reaction mixture was refluxed for a further 1.25 hours. It was then stirred at room temperature overnight (17.5 hours) and an extra 2.5 mL (31.2 mmol, 0.61 equiv.) of thiophene was added. After heating under reflux for 4 hours the reaction was quenched with water, filtered, and the product extracted with methylene chloride. After drying over anhydrous sodium sulfate and filtering, the solvent was stripped on a rotary evaporator. The crude product 6.39 g) was dried at the pump and analyzed by NMR ISTD. The purity was indicated to be 40.7%, the product yield was therefore 20.9%.

EXAMPLE 9 - (COMPARATIVE)

Acylation of Thiophene With 2-Phenyl-5-oxazolone With Normal Catalyst Addition In Methylene Chloride A 500 mL, round-bottomed, 3-necked flask was charged with 10.03 g (62.05 mmol) of 2-phenyl-5-oxazolone, 6.0 mL (74.95 mmol, 1.21 equiv.) of thiophene, and 200 mL of dried methylene chloride. The orange solution was stirred under a nitrogen atmosphere with ice bath cooling for 30 minutes. The gradual addition of 16.58 g (2.00 equiv.) of aluminum chloride was then carried out over a 1.5 hour period. After 1 hour at 3°–4° C. an additional 0.5 mL (6.25 mmol, 0.1 equiv.) of thiophene was added and the reaction mixture was stirred overnight (15 hours) at room temperature. The reaction was then quenched with water, filtered, and the product extracted with methylene chloride. After drying over anhydrous sodium sulfate and filtering the solvent was stripped on a rotary evaporator. The crude product (13.85 g) was dried at the pump and analyzed by NMR ISTD. The purity was indicated to be 42.7% and the product yield was therefore 38.8%.

EXAMPLE 10

Preparation of 2-(2-Thienyl)-ethylamine and N-Benzoyl-2-(2-Thienyl)ethylamine

A 25 mL, round-bottomed, 2-necked flask was charged with 4 mL of diethylene glycol, 0.62 g of potassium hydroxide, and 0.41 g of 85% hydrazine hydrate. The reaction mixture was stirred well for 10 minutes, then 1.02 g of α-N-benzoylamioo-2-acetyl thiophene was added. The reaction mixture was heated to reflux (bath 165°–190° C.) for 1.5 hours. GC analysis indicated the presence of 62% N-benzoyl-2-(2-thienyl)-ethylamine, and 22% 2-(2-thienyl)-ethylamine. Identification was made by GC/mass spectrometry and chromatographic comparison with authentic samples.

EXAMPLE 11

Acid Hydrolysis of α-N-benzoylamino-2-acetylthiophene

A 25 mL, round-bottomed, single-necked flask was charged with 1.0 g of α-N-benzoylamino-2-acetylthiophene, 7.5 mL of concentrated hydrochloric acid and 7.5 mL of water. The reaction mixture was heated under reflux (bath temperature 130° C.) for 8 days. It was then cooled and filtered, and the collected solids were washed with 1N hydrochloric acid. The combined aqueous layer was washed with methylene chloride and then stripped on a rotary evaporator. After drying at the pump, α-amino-2-acetylthiophene hydrochloride was collected as a crystalline solid in 75% yield (0.5 g).

EXAMPLE 12

Reduction of α-amino-2-acetylthiophene Hydrochloride

A 25 mL, round-bottomed, 2-necked flask was charged with 0.2 g of α-amino-2-acetylthiophene hydrochloride and 15 mL of diethyl ether, and the reaction mixture was saturated with hydrogen chloride gas at 0° C. To this was added in portions 1.0 g of activated (acid washed) zinc powder over a 30 minute period. The reaction mixture was stirred for an additional 20 minutes and then quenched by adding to iced water and gasified by the addition of sodium hydroxide. The product was extracted using diethyl ether and shown by GC to contain 2-(2-thienyl)-ethylamine to the extent of 57%.

EXAMPLE 13

Acylation of Thiophene With 2-(4-Methylphenyl)-5-oxazolone

A 250 mL, round-bottomed, 3-necked flask was charged with 5.0 g (28.5 mmol) of 2-(4-methylphenyl)-5-oxazolone, and 100 mL of dried methylene chloride, and cooled in an ice bath under a nitrogen atmosphere. Using a powder addition funnel, 7.61 g of aluminum chloride was added over a period of 15 minutes to the stirred reaction mixture. After holding for 10 minutes the gradual addition of thiophene (2.75 mL) was carried out over a 15 minute period. The reaction mixture was then stirred for 75 minutes at 3°–4° C., after which time an additional 0.2 mL of thiophene was added. The reaction mixture was then stirred for an extra 20 minutes at the same temperature, and was then quenched by its addition to iced water. The product was extracted several times with methylene chloride, and the combined extracts were dried over anhydrous sodium sulfate, filtered, then stripped on a rotary evaporator. After drying at the pump the crude product (7.32 g) was analyzed by NMR internal standard method and found to be 48.1% pure. The product yield was therefore 47.5%.

The substituted hippuric acid (mp 167°–168° C.) used in this reaction was prepared by the acylation of glycine with 4-toluoyl chloride by a modification of a literature procedure [Steiger, R. E. *J. Org. Chem.*, (1944), 9, 396]. The corresponding azlactone was made by treatment of the acid with acetic anhydride as described above for 2-phenyl-5-oxazolone.

EXAMPLE 14

Acylation of Thiophene With 2-(2-Chlorophenyl)-5-oxazolone

The procedure of Example 13 was followed except 2-(2-chloro- phenyl)-5-oxazolone was substituted for 2-(4-methylphenyl)-5-oxazolone to yield α-N-(2-chlorobenzoylamino)-2-acetylthiophene.

EXAMPLE 15

The reaction of Example 13 was followed substituting 2-(4-tert-butylphenyl)-5-oxazolone as the acylating compound to produce α-N-(4-tert-butylbenzoylamino)-2-acetylthiophene.

EXAMPLE 16

The reaction of Example 13 was followed except that 2-(2-methylphenyl)-5-oxazolone was substituted as the acylating compound to produce α-N-(2-methylbenzoylamino)-2-acetylthiophene.

EXAMPLE 17

The reaction of Example 13 was followed substituting 2-(3-trifluoromethylphenyl)-5-oxazolone as the acylating compound to produce α-N-(3-trifluoromethylbenzoylamino)-2-acetylthiophene.

What is claimed is:

1. A process for the preparation of 2-(2-thienyl)-ethylamine derivatives having the formula:

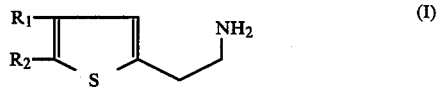

wherein $R_1$ and $R_2$ are hydrogen or taken together form a phenyl ring comprising:

(a) reacting a derivative having the formula:

with a mixture of an acylating compound selected from the group consisting of:

$$(R_3)_n C_6 H_{5-n} CONHCH_2 COCl, \text{ and} \quad (i)$$

$$(R_3)_n C_6 H_{5-n} C = NCH_2 COO; \quad (ii)$$

wherein $R_3$ is selected from the group consisting of $C_{1-4}$ lower alkyl, $C_{1-4}$ lower alkoxy, phenoxy, $NO_2$, $CF_3$, Cl, Br, I and F, and n=0 to 3, and an acylating catalyst to give a derivative having the formula:

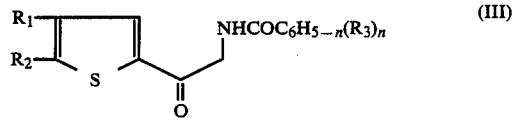

(b) reducing and hydrolyzing the derivative of formula (III) to give the derivative of formula (I).

2. The process as defined in claim 1 wherein the derivative of formula (I) is 2-(2-thienyl)-ethylamine.

3. The process as defined in claim wherein the acylating compound is 2-phenyl-5-oxazolone.

4. The process as defined in claim 1 wherein the acylating compound is hippuryl chloride.

5. The process as defined in claim 1 wherein the acylation catalyst is a Lewis acid catalyst 6. The process as defined in claim 5 wherein the acylation catalyst is $AlCl_3$.

7. The process as defined in claim 1 wherein the reduction and hydrolysis in step (b) are performed simultaneously in the presence of hydrazine under basic conditions.

8. The process as defined in claim 1 wherein the reduction in step (b) is performed prior to the hydrolysis in step (b).

9. The process as defined in claim 1 wherein the hydrolysis in step (b) is performed prior to the reduction in step (b).

* * * * *